United States Patent [19]

Kemeny et al.

[11] Patent Number: 5,039,855
[45] Date of Patent: Aug. 13, 1991

[54] DUAL BEAM ACOUSTO-OPTIC TUNABLE SPECTROMETER

[75] Inventors: Gabor J. Kemeny, Peekskill; Carl G. Soryn, Pound Ridge; Howard Mark, Suffern; Robert E. Rachlis, Chappaqua, all of N.Y.; James Evans, Stamford, Conn.; Aamir Ashraf, Flushing, N.Y.

[73] Assignee: Bran+Luebbe Analyzing Technologies, Inc., Elmsford, N.Y.

[21] Appl. No.: 488,687

[22] Filed: Mar. 5, 1990

[51] Int. Cl.$^5$ .............................................. G01N 21/00
[52] U.S. Cl. .................................. 250/339; 250/343; 356/437; 350/358
[58] Field of Search .................. 250/345, 343, 339; 356/436, 437; 350/358, 370

[56] References Cited

U.S. PATENT DOCUMENTS

| | | | |
|---|---|---|---|
| 3,520,614 | 7/1970 | Goldstein | 356/97 |
| 3,566,119 | 2/1971 | Lewis | 250/522.1 |
| 3,679,288 | 7/1972 | Harris | 350/149 |
| 3,828,173 | 8/1974 | Knepler | 235/151 |
| 3,861,788 | 1/1975 | Webster | 350/315 |
| 3,900,851 | 8/1975 | Bucy et al. | 350/358 |
| 3,944,335 | 3/1976 | Saito et al. | 350/161 |
| 3,953,107 | 4/1976 | Yano et al. | 350/149 |
| 4,052,121 | 10/1977 | Chang | 350/149 |
| 4,082,464 | 4/1978 | Johnson, Jr. | 356/188 |
| 4,236,076 | 11/1980 | Judge et al. | 250/347 |
| 4,264,205 | 4/1981 | Landa | 356/326 |
| 4,285,596 | 8/1981 | Landa | 356/308 |
| 4,286,327 | 8/1981 | Rosenthal et al. | 364/498 |
| 4,342,502 | 8/1982 | Chang | 350/358 |
| 4,404,642 | 9/1983 | Rosenthal | 364/571 |
| 4,540,282 | 9/1985 | Landa et al. | 356/328 |
| 4,602,342 | 7/1986 | Gottlieb et al. | 364/498 |
| 4,663,961 | 5/1987 | Nelson et al. | 73/24 |
| 4,722,596 | 2/1988 | Labrum et al. | 350/358 |
| 4,736,103 | 4/1988 | Nelson et al. | 250/339 |
| 4,883,963 | 11/1989 | Kemeny et al. | 250/339 |
| 4,945,539 | 7/1990 | Bagshaw et al. | 372/20 |

OTHER PUBLICATIONS

Harris et al., "Acousto-Optic Tunable Filter", Journal of the Optical Society of America, vol. 59, No. 6, pp. 744-747, (6/89).
Chang, "Non-Collinear Acousto-Optic Filter with Large Angular Aperture", Applied Physics Letters, vol. 25, No. 7, pp. 370-372, (10/77).
Wetzel, "Near-Infrared Reflectance Analysis", Analytical Chemistry, vol. 55, No. 12, (10/83), (Background article concerning the use of near infrared analysis).

Primary Examiner—Carolyn E. Fields
Assistant Examiner—Drew A. Dunn
Attorney, Agent, or Firm—Davis Hoxie Faithfull & Hapgood

[57] ABSTRACT

A dual beam acousto-optic tunable spectrometer utilizes an optics system to isolate the two radiation beams tuned by an acousto-optic filter, one of which is used to analyze a sample, the other of which is used as a reference. The tuning of the filter and the analysis of the signals is conducted by a microprocessor, which corrects for the many possible sources of noise. A new fluid sample cell utilizing glass balls to collimate radiation incident on the sample and focus radiation transmitted from the sample, is also disclosed.

37 Claims, 11 Drawing Sheets

FROM CONTROLLER 300

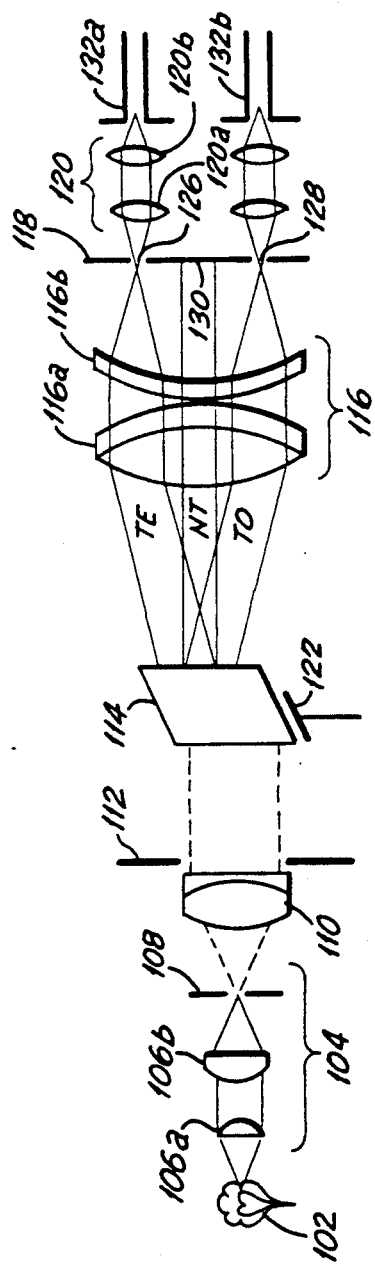
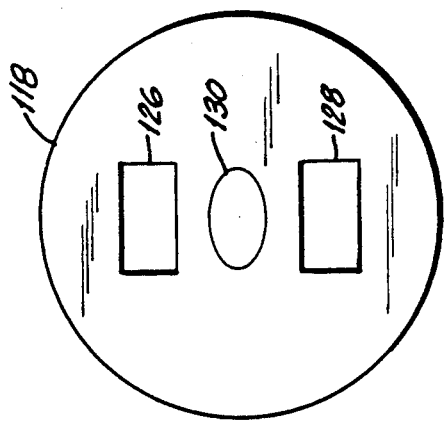
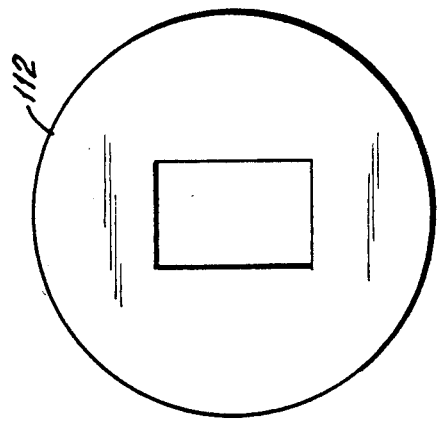
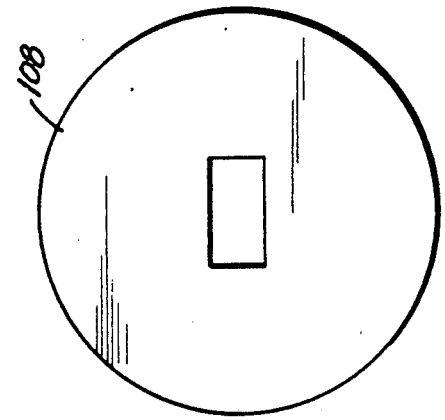
FIG. 3
FIG. 3a
FIG. 3b
FIG. 3c

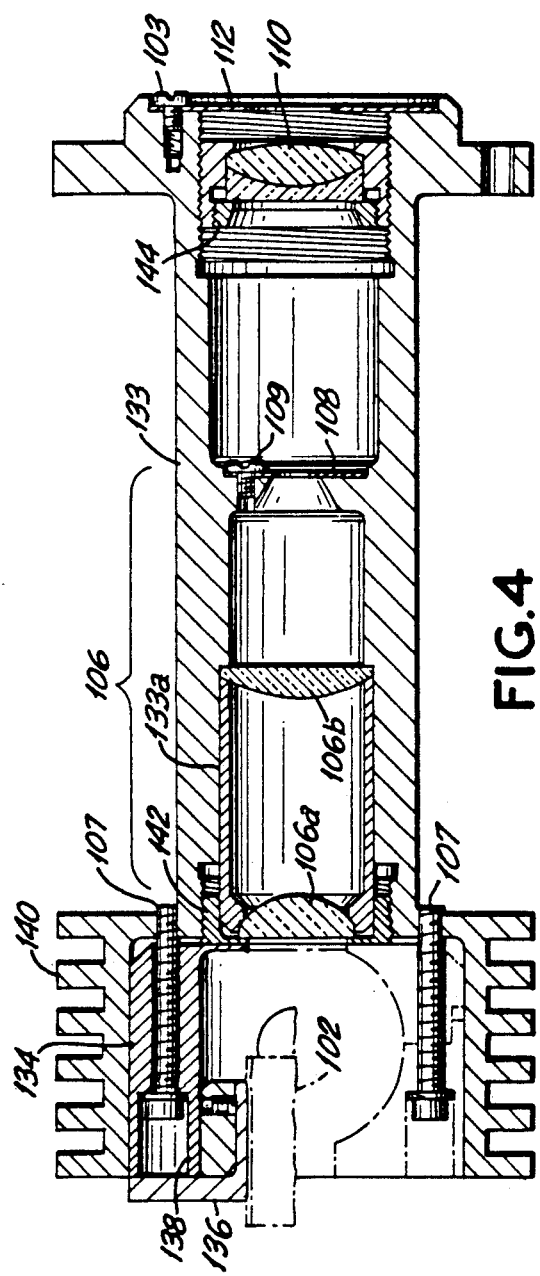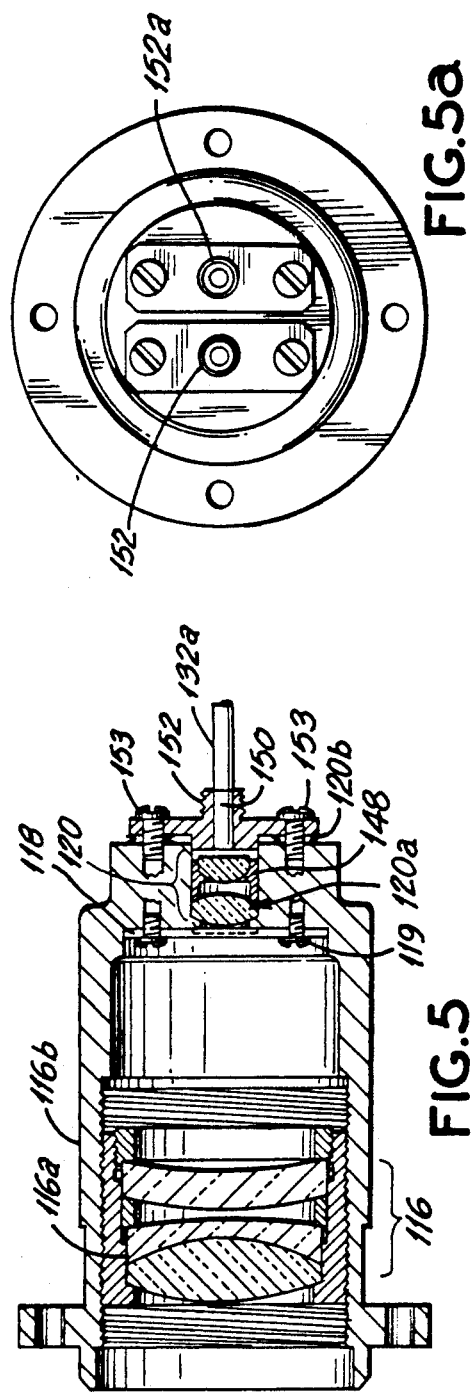

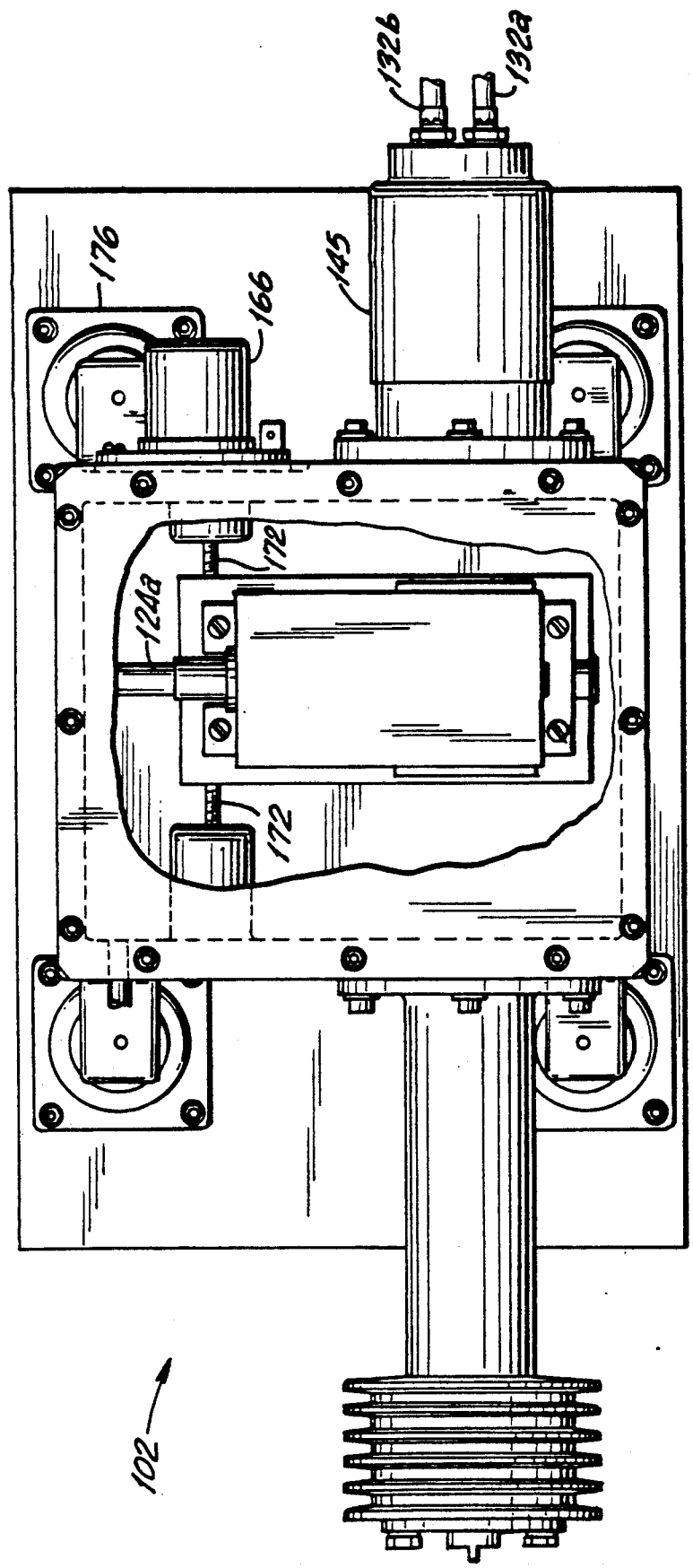

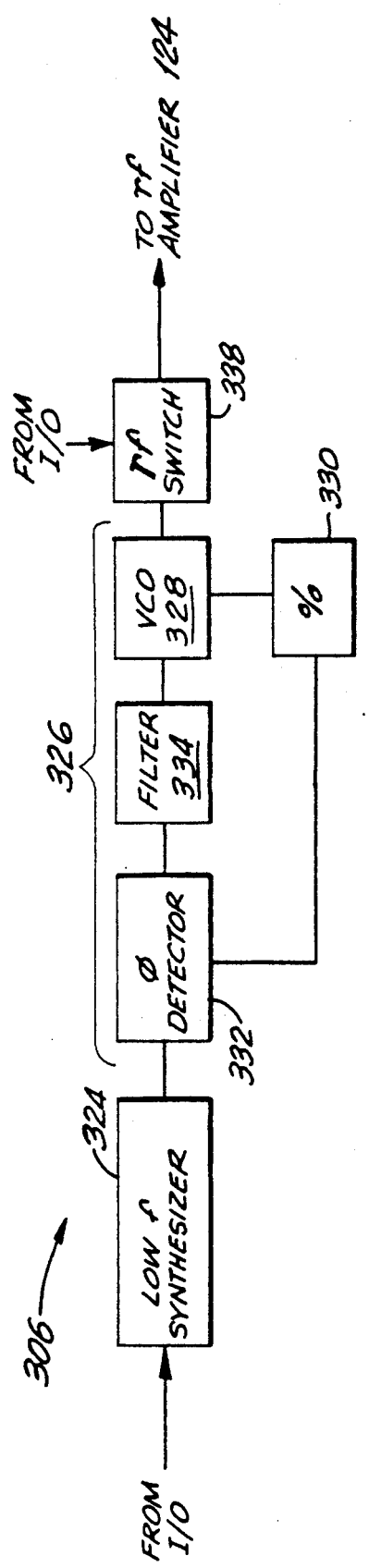
FIG.11a
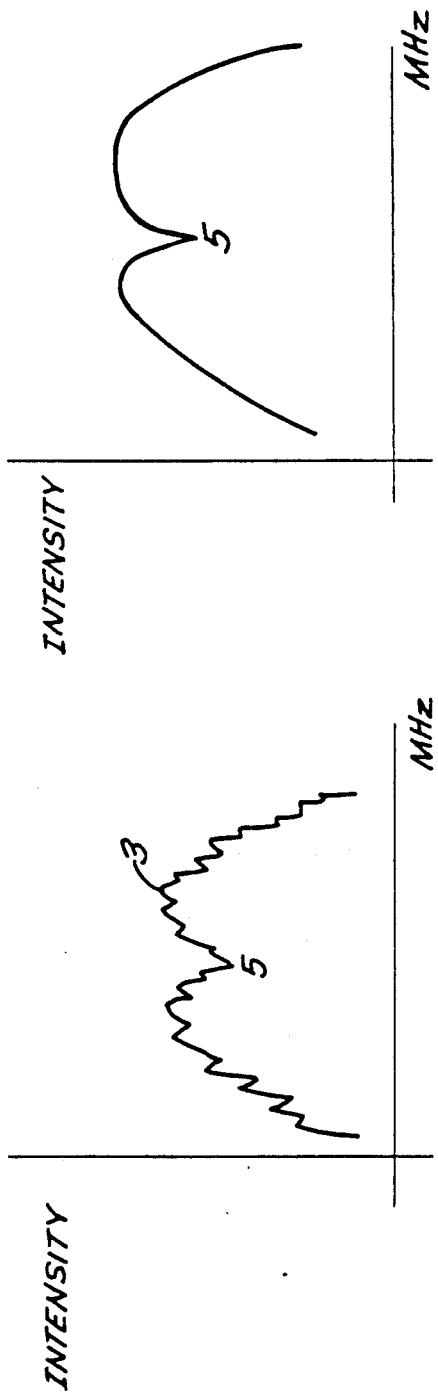
FIG.12a
FIG.12

DUAL BEAM ACOUSTO-OPTIC TUNABLE SPECTROMETER

FIELD OF INVENTION

The present invention relates to an acousto-optic tunable analyzer and, more particularly, a dual beam acousto-optic tunable spectrometer for use in analyzing the constituent composition of a sample.

BACKGROUND OF THE INVENTION

Infrared analyzing devices have been used to identify and analyze the concentrations of components of samples based on their absorbance at particular wavelengths. For example, the starch, protein, lipid and fiber concentrations of grains, the octane number of gasoline, the moisture content of chemicals or foods, or the lignin content of pulp and paper, can be determined through infrared analysis. While most analyzing systems are adapted for use in a laboratory, the on-site and in-line monitoring of industrial processes is an important application of this technology. In in-line monitoring, the samples are usually moving and may be inhomogeneous. Their composition and optical characteristics may change suddenly. Measurements need to be performed rapidly and a large number of such measurements may need to be averaged to correct for discontinuities in the sample or other sources of error. While a flowing sample may be stopped in a sample cell long enough to test, such a sample may not be representative of the bulk of the product stream and the testing process may be too slow for most control monitoring purposes.

Noise is a common problem effecting the accuracy of absorbance measurements. Common sources of noise are fluctuations in the emission of the radiation source, heat, degradation of system components, power fluctuations and other random variations due to internal or external causes. To correct for noise, measurements of a sample and a reference are taken and compared. If the measurements are made close enough in time, noise which effects the sample reading will also effect the reference reading and can be cancelled.

Of the two main types of analysis devices, the dual beam and single beam, only the dual beam device can simultaneously measure the sample and reference. It does this by splitting the incident radiation with a mirror, for example, and directing one beam to the sample and the other to the reference. In a single beam device the incident radiation is alternatively applied to the sample and reference by a rapidly switching mirror. Since the reference should indicate the signal level to be compared with the sample measurement, the faster the switching the more accurate the correction.

Because of their better error correction, dual beam systems are more precise than single beam systems. They require complex optics systems, however, and are therefore more expensive. The single beam system is simpler and easier to use and maintain, but is less precise. The precision of the single beam system can be improved by increasing the switching rate of the mirror, but this adds to the complexity and cost of the system. In U.S. Pat. No. 4,236,076, to Judge and assigned to Alfa-Laval AB, the precision of a single beam system is improved without adding complexity to the system through a unique averaging technique.

To determine the absorbance of a sample at a specific wavelength, the wide-band radiation emitted by a source, such as a tungsten-halogen lamp, needs to be filtered. Various mechanical methods have been employed to switch between the many filters required to shift from wavelength to wavelength during an analysis. One method is to mount a series of filters on a rotating turret or a paddle wheel. See, for example, U.S. Pat. Nos. 4,236,076 and 4,082,464. Since the sequential change in wavelength is limited by the speed of the shifting filters, analysis is too slow for in-line concentration monitoring in many manufacturing or production processes.

To increase the speed of analysis, infrared emitting diodes ("IREDs") controlled by a microprocessor have been utilized. See, for example, U.S. Pat. No. 4,401,642. Such systems can only analyze across a limited bandwidth, however, due to the limited range of IREDs (850-1050 mm). Another approach is to use vibrating holographic gratings. See, for example, U.S. Pat. No. 4,540,282. While the speed of analysis is increased, it is difficult to correct for errors.

The fastest switching between wavelengths for analysis can be achieved by an acousto-optic tunable filter, which is a crystal whose index of refraction can be altered by acoustic waves. The application of a particular frequency of acoustic wave to a birefringent crystal changes the direction of propagation and the polarization of a narrow wavelength band of the incident radiation, yielding two tuned radiation beams which diverge from each other and the non-tuned radiation. The tuned wavelength can be isolated and used to analyze a sample. The tuned wavelength band can be changed in milliseconds, depending on the speed of other components of the system. One commonly used crystal is tellurium dioxide. AOTFs are described in Harris, et al., "Acousto-Optic Tunable Filter", Journal of the Optical Society of America, Vol. 59, No. 6, pp. 744-747 (June 1969); Chang, "Noncollinear Acousto-Optic Filter With Large Angular Aperture", Applied Physics Letters, Vol. 25, No. 7, pp 370-372 (10/1977); and U.S. Pat. Nos. 3,679,288; 3,944,334; 3,944,335; 3,953,107; 4,052,121 and 4,342,502, which are incorporated by reference herein.

In U.S. Pat. No. 4,883,963 to Kemeny et al. and assigned to the assignee of the present invention, a birefringent AOTF is used in an in-line monitoring system for rapid analysis of a moving or changing sample. A variety of scanning patterns are shown.

In U.S. Pat. No. 4,602,342 to Gottlieb et al., an AOTF of mercurous chloride and related crystals is disclosed for use in an analysis system which utilizes one or two polarizers to isolate one tuned beam. In U.S. Pat. No. 4,663,961 to Nelson et al., optical fibers are used to carry radiation to and from a birefringent AOTF. This system also isolates one tuned beam through polarizers.

To determine a baseline, the Gottlieb and Nelson systems measure the response of an empty sample cell. Measurements of actual samples are then compared to the reference. It appears that only one reference measurement is used to correct all future sample tests. Since the reference measurement is not close in time to the sample measurements, noise and drift affecting the sample measurement may not be corrected. Fluctuations occurring after the reference test is run cannot be compensated for.

SUMMARY OF THE INVENTION

The present invention provides an acousto-optic tunable spectrometer which overcomes the deficiencies of prior systems. The spectrometer of the present invention isolates the two diverging tuned radiation beams created by a birefringent AOTF from each other and the non-tuned radiation, and uses one beam to analyze a sample and the other as a reference. The two measurements are then compared to correct the sample measurement for noise. Due to its speed and precision the system is particularly suited for use in in-line monitoring.

A dual beam acousto-optic tunable spectrometer according to the present invention comprises a birefringent acousto-optic tunable filter. There are means for driving the acousto-optic tunable filter at a desired frequency to tune incident radiation, yielding a first and second beam which diverge from each other and the non-tuned radiation. There are means for collecting the first tuned beam for use in analyzing a sample and means for collecting the second tuned beam for use as a reference.

The acousto-optic tunable spectrometer of the present invention also comprises a radiation source and means for collimating radiation from the radiation source. The radiation is incident on an acousto-optic tunable filter. There is a means for driving the acousto-optic tunable filter at particular frequencies to tune desired narrow bandwidths of the incident radiation. The tuned bandwidth forms first and second tuned beams which diverge from each other and the radiation outside the narrow bandwidth. There is a means for conveying the first tuned beam to a sample for analysis. A first detector means is provided for detecting the first tuned beam after exposure to the sample and a second detector means is provided for detecting the second tuned beam for use as a reference. There is a means for conveying the second tuned beam to the second detector. There is an analyzing means and means for inputing signals from the first and second detecting means to the analyzing means.

An optics system preferably collimates the radiation from a source before it enters the AOTF. A condensing system can be used to collect radiation from the source, which can then be exposed to an aperture which limits the angular divergence of the radiation incident on the AOTF. A collimating lens can be followed by another aperture, which establishes the boundaries of the radiation which will be incident on the AOTF.

Behind the AOTF, an achromatic lens system can be used to focus the two tuned beams on two symmetrical apertures. The nontuned beams are blocked. A condensing system behind each aperture focus can be used to the tuned beams into two optical fibers, one for conveying one tuned beam to a sample cell to analyze the sample, the other for conveying the other tuned beam directly to a detector.

The sample cell, which is also a subject of the present invention, receives one tuned beam from an optical fiber and applies it to a sample in an analysis area. The tuned beam emerging from the optical fiber is collimated by a first glass ball before being exposed to the sample. A second glass ball focuses the radiation transmitted and scattered by the sample onto another optical fiber, which carries the radiation to a detector.

A controller, comprising a microprocessor, analyzes the sample and reference beam to determine the absorbance at a particular wavelength. The microprocessor also drives the acousto-optic tunable filter at specific frequencies to yield specific tuned wavelengths. The controller can utilize a low frequency synthesizer and a phase lock loop containing a high frequency voltage controlled oscillator and a divider circuit to generate the actual driving frequencies. The microprocessor provides corrections for errors, including temperature deviations, through its scanning pattern and frequency generation.

DESCRIPTION OF THE DRAWINGS

FIG. 3 is a schematic view of the optics system of the present invention;

FIG. 3a is a front view of the first aperture of the optics system shown in FIG. 3;

FIG. 3b is a front view of the second aperture of the optics system shown in FIG. 3;

FIG. 3c is a front view of the disc used in the optics system shown in FIG. 3, including the first and second tuned apertures and the darkspot;

FIG. 4 is a cross-sectional view of the actual condenser and collimator system used in the present invention;

FIG. 5 is a cross-sectional view of the actual exit optics system used in the present invention;

FIG. 5a is a front view of the back of the exit optic system, showing the optical fiber connectors;

FIG. 6b is a top view of the assembled optics system shown in FIG. 6, with part of the top of the acousto-optic filter housing removed;

FIG. 11a is a schematic diagram of the rf synthesizer shown in FIG. 11;

FIG. 12 is a graph of frequency versus intensity, showing acoustic resonance; and FIG. 12a is a graph of frequency versus intensity without acoustic resonance.

DETAILED DESCRIPTION OF THE INVENTION

Figure 1:
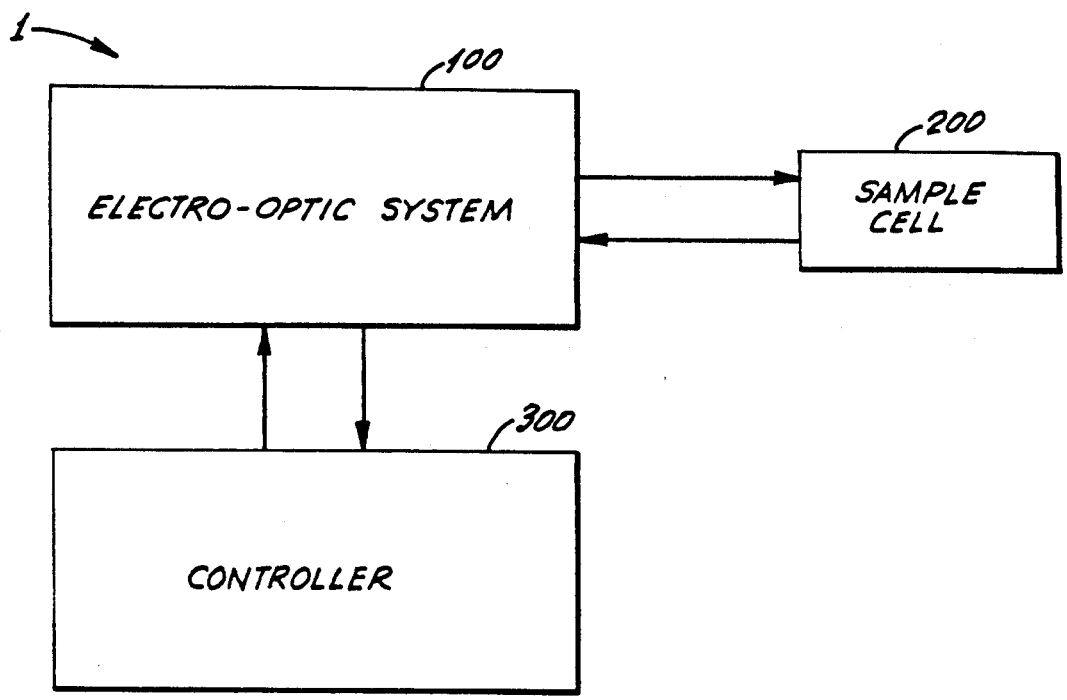
FIG. 1 is a schematic diagram of the major elements of the acousto-optic tunable spectrometer of the present invention.
Figure 2:
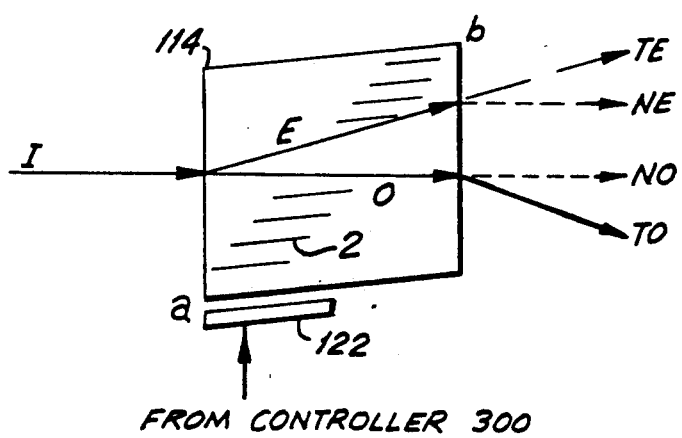
FIG. 2 is a schematic diagram of the tuning of incident radiation by a birefringent acousto-optic filter.

The acousto-optic tunable spectrometer ("AOTS") 1 of the present invention comprises an electro-optic system 100, a sample cell 200 and a controller 300, as shown schematically, in FIG. 1. The AOTF 114 is shown schematically in FIG. 2 as a parallelogram. The AOTF 114 is a non-collinear device, preferably comprising a birefringent crystal of tellurium dioxide (TeO$_2$). AOTFs used in the present invention are available from Crystal Technology, Inc. a division of Siemens, or AOTF Technology, Inc. Tellurium dioxide is preferred because it has a high figure of merit for acousto-optic interaction and propagates shear acoustic waves slowly. The high figure of merit and slow propagation enables a low driving frequency. Other crystals can also be used, such as lithium niobate or quartz. One or more piezo-electric transducers 122 of lithium niobate, for example, generate acoustic shear waves 2 through the crystal. The acoustic waves travel from the lower left corner "a" of the AOTF to the upper right corner "b". In a non-collinear device, the incident radiation is nearly perpendicular to the acoustic wavefronts. The transducers 122 are driven by the controller 300, which is discussed in more detail, below.

When parallel rays of incident radiation I pass through the AOTF 114, the birefringent character of the crystal polarizes the radiation into an ordinary beam "O", which travels straight through the crystal, and an extraordinary beam "E", which is refracted at a small angle from the ordinary beam 0. This is shown exaggerated in FIG. 2. In addition, it is believed that the acoustic shear waves 2 generated in the crystal cause an elasto-optic interaction with the crystal which rotates the principal planes of the index of refraction of the crystal, at particular wavelengths. This causes the polarization of a narrow wavelength band of the 0 beam to match that of the E beam and the polarization of the same wavelength band of the E beam to match that of the 0 beam. The bandwidth can be about 3-15 nanometers and the specific bandwidth beam is referred to as "tuned". The tuned bandwidth is dependent on the frequency of the acoustic driving wave and the design of the crystal.

Upon exiting the crystal, the non-tuned bandwidths of the 0 beam continues unrefracted, as indicated by the arrow "NO". The non-tuned bandwidths of the E beam refract to their original direction, parallel with the incident beam, as indicated by the arrow "NE". The tuned bandwidths of the E and 0 beams, in contrast, are refracted about 6-8 from the incident beam, as indicated by the arrows "TE" and "TO". Therefore, two independent tuned beams of the same, narrow bandwidth, exit from the crystal about 12-16° apart. Each tuned beam diverges about 6-8° from the non-tuned light.

Either of two different crystals can be used in the present invention, one to tune in the 800-1,400 nm range and the other to tune in the 1,100-2,500 nm range. A driving frequency of between 40-80 MHz is required to tune the longer wavelengths while 90-150 MHz is required to tune the shorter wavelengths. The AOTF crystal yields background energy less than about 1% of the tuned energy.

The Electro-optic System

The unique dual beam acousto-optics system 100 of the present invention, shown schematically in FIG. 3, isolates both of the tuned beams discussed above. The system preferably comprises a source of infrared radiation 102, a condensing system 104 including an aperture 108, a collimating means 110, a second aperture 112, the acousto-optical tunable filter 114 in a module 158, an achromatic lens system 116, a disc 118 and a pair of condensing systems 120.

The radiation source is preferably a standard tungsten halogen light bulb 102. If the system is operating between about 1.5-2.5 microns, it is preferred that the bulb include a gold plated concentric reflector to increase the emission characteristics of the bulb, as described in U.S. Pat. No. 4,346,383 to Hirschfield and, assigned to Alfa-Laval AB. At shorter wavelengths, it has been found that the reflector is not necessary.

The radiation emitted by the tungsten bulb 102 preferably passes through the condenser system 104 comprising a pair of plano-convex lens 106a and 106b with a magnification ratio of two to one. Suitable lenses are LPX 017 and LPX 063 from Melles Griot, Inc. The lenses focus the light from the tungsten lamp 102 toward an aperture 108 having a rectangular shape, as shown in FIG. 3a. The aperture is 2mm×4mm. The long axis of the aperture is essentially parallel to the direction of the driving acoustic wave. The aperture 108 establishes the angular divergence of the light beam which will be incident upon the AOTF 114. The size of the aperture 108 is dependent on the angle of diffraction of the tuned beams emitted from the AOTF 114 and is set so that the tuned beams TE and TO emitted by the AOTF 114 are isolated from the unrefracted, non-tuned radiation indicated as "NT" in FIG. 3. The angle of diffraction of the AOTF used is about 6-8.

A collimating lens 110 is preferably provided to collimate the radiation passing through the aperture 108 before the radiation enters the AOTF 114. It is essential that the lens be clean, scratch free and bubble free, to minimize the scattering of light entering the AOTF 114. The lens is an F2, achromatic doublet with a 40 mm focal length, and an 18 mm diameter, available from Melles Griot, model number 01 LA0037. It is positioned about 36mm from the aperture 108. Instead of a collimating lens, it is possible to extend the length of the light path between the aperture 108 and the AOTF 114 so that the radiation is essentially parallel. Furthermore, it is possible to dispense with the condensing system and place the lamp 102 in the position of the aperture 108 in less rigorous applications.

A second aperture 112 is placed behind the collimating lens 110 for defining the boundaries of the radiation beam entering the AOTF 114. The size of the beam should be slightly less than the size of the crystal, so that the light does not scatter off any surfaces into the AOTF 114. The dimensions of this aperture are 7mm×11mm. The dimensions of the entrance to the AOTF module 158 are 8mm×12mm. A front view of the second aperture is shown in FIG. 3b.

The radiation exiting the AOTF crystal 114 passes through the achromatic lens system 116 comprising an achromatic objective lens 116a and an aplanatic meniscus lens 116b separated by air. The diameters of the lenses are 30mm which is large enough to collect the tuned beams. The lenses need to be fast and therefore have a low F number. The selected system is F2, where the focal length is twice the diameter. The front focus of the lens is essentially in the exit plane of the crystal, so that the main ray of the system emerges from the lenses parallel to the optical axis of the system. The first lens is about 45 mm from the end face of the crystal. These lenses are also available from Melles Griot, model numbers 01 LAO 7a and 01 LAM 155, respectively.

The non-tuned beam is focused by the lens along the optical axis of the system, while the two tuned beams are symmetrically focused on opposite sides of the optical axis. Each beam forms an image of the aperture 108. The disc 118 includes two tuned beam apertures 126 and 128, having the same dimensions as the aperture 108, as shown in FIG. 3c. One tuned beam is focused on each stop. At the center of the post-filter field stop is a darkspot 130 which is painted optical black with, for example, NEXTEL TM C101 from 3M. The non-tuned radiation is focused onto the darkspot 130 where it is absorbed. The tuned beam apertures should be symmetrically disposed about the optical axis of the system, essentially in the plane in which the acoustic waves are applied. The field stop 118 is positioned 35 mm behind the lens 116b.

Behind each field stop 126, 128 is a small condenser system 120 comprising a symmetrical convex lens 120a and plano-convex lens 120b. These lens focus the tuned beam into optical fibers 132a and 132b. The optical fibers are preferably low OH, to minimize absorbtion of infrared radiation by the fiber itself. Such fibers are available from Fiberguide Industries, Inc., for example.

The ability to independently collect each of the tuned beams by focusing each beam on separate apertures is an important feature of the present invention. It avoids the need for polarizers, as in the prior art, to filter out the beams which are not to be used in analysis. Polarizers are expensive and their use with a birefringent crystal eliminates half of the energy useful for analysis. By utilizing the second tuned beam, which follows a nearly identical optical path as the analyzing beam, better correction for noise can be achieved than in the prior art, at lower cost.

The actual condenser and collimator system used is shown in cross-section in FIG. 4, with corresponding elements of FIG. 3 numbered the same. In FIG. 4, which is rotated 90° about the optical axis from the orientation in FIG. 3, there is a system housing 133 which supports the components. A lamp holder 134 is provided for the lamp 102. A lamp mount 136 secures the lamp, whose position can be varied by a center adjuster 138. Heat dissipating fins 140 surround the exterior of the lamp holder 134 to prevent overheating of the lamp. A retainer 142 lies between the lamp holder 134 and the condenser 106, which are bolted together by bolts 107. The collimating lens 110 lies in a retainer 144, which is screwed into the housing 133 at 133a. The position of the lens can be adjusted by rotating the retainer. The bolt 109 secures the first aperture 108 to the interior of the housing 133, while the bolt 113 secures the second aperture 112.

FIG. 5 shows the optical system behind the AOTF 114, referred to as the exit optical system 145, which is also rotated 90° about the optical axis from the orientation in FIG. 3. The achromatic lens 116 lies in a retainer 146, whose position is adjustable by rotation in the same manner as the collimating lens 110. The condenser system 120 lies in a stationary retainer 148. Bolts 119 secure the post-filter back stop in place.

The condensing system 120 focuses the incident tuned beam into the region 150, which leads to an optical fiber adaptor 152, which connects to the optical fiber 132a. The second condensing system and optical fiber assembly lie behind the one shown in FIG. 5. FIG. 5a is a view of the back of the optical system of FIG. 5, showing the two fiber optic connectors 152 and 152a.

Figure 6:
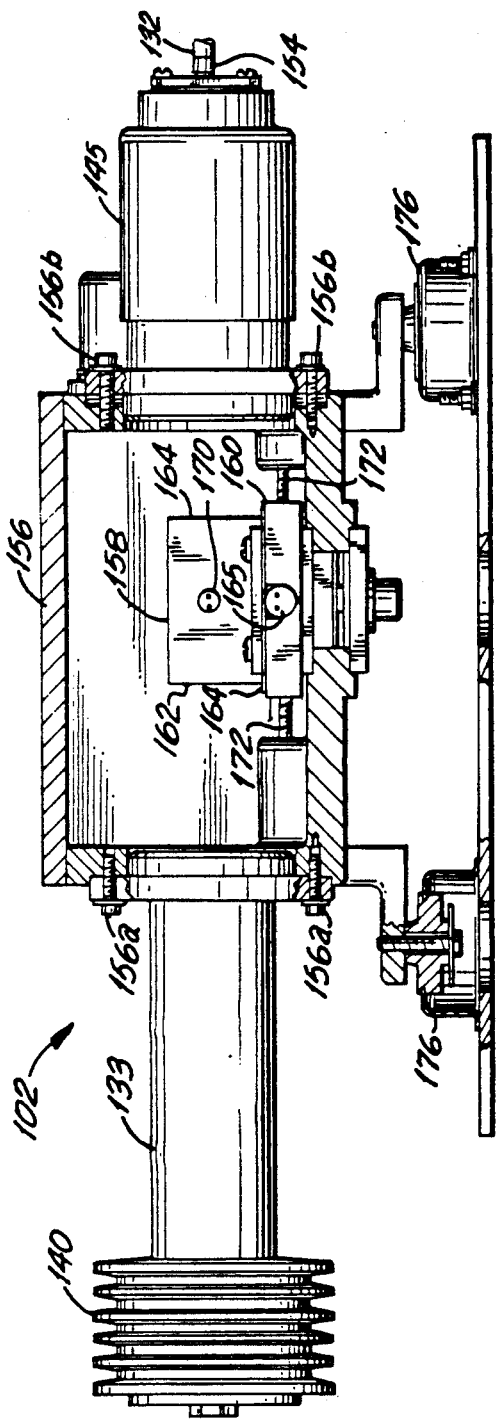
FIG. 6 is a side view of the assembled optics system of the present invention, with the acousto-optic tunable filter housing shown in cross-section.
Figure 6A:
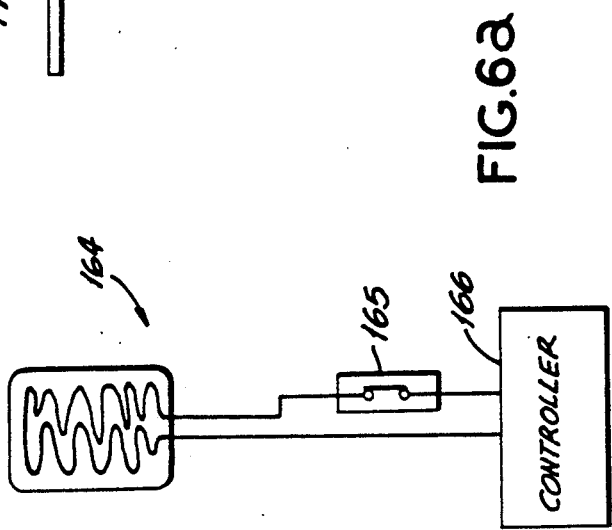
FIG. 6a is a view of the heater used in the present invention.
Figure 7:
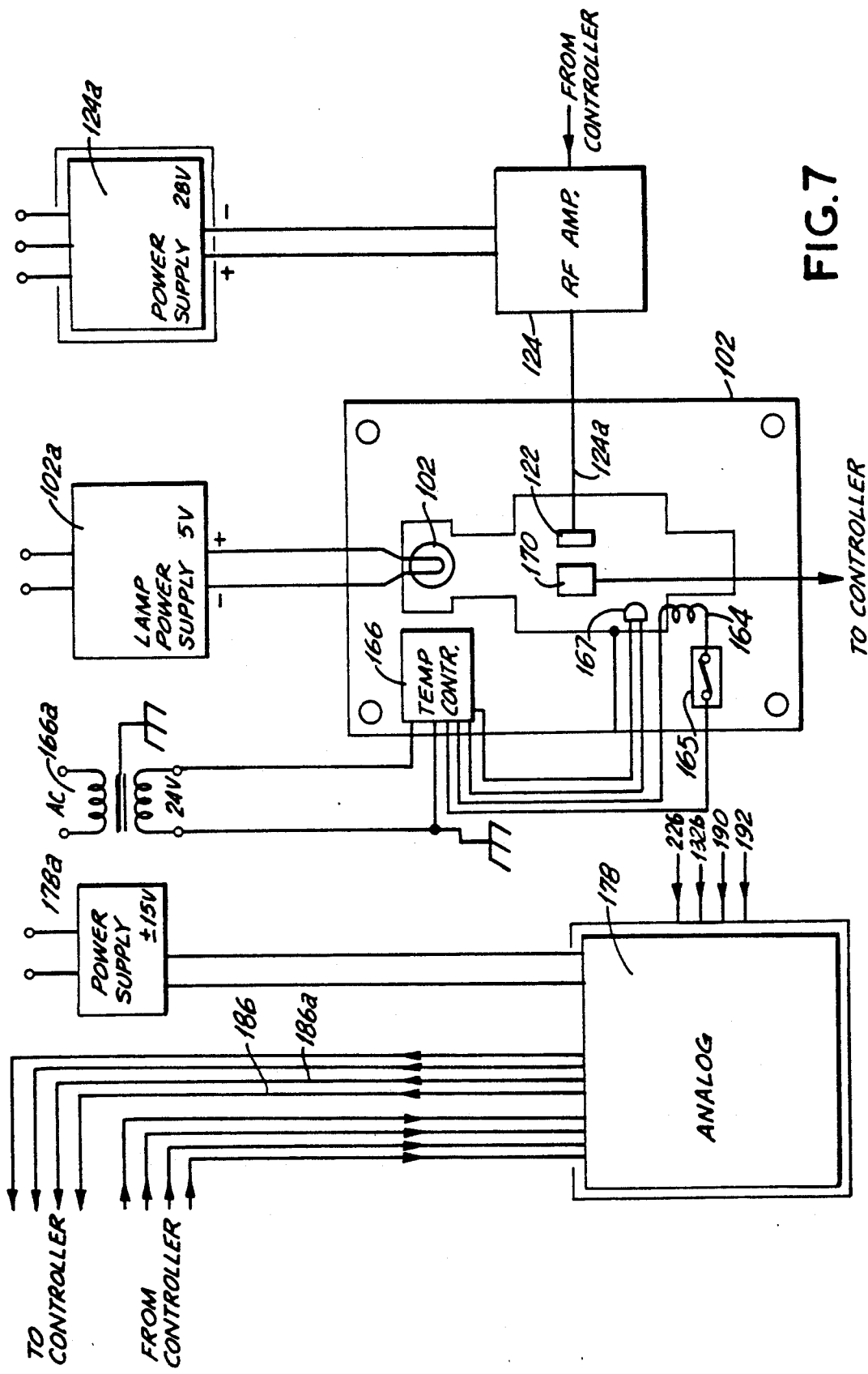
FIG. 7 is a schematic diagram of the electrical system of the electro-optic section.

Bolts 153 secure the connectors 152 and 152a in place. FIG. 6 is a side view of the acousto-optic system 102, showing the exterior of the condenser/collimator system housing 133 and the exterior of the exit optical system 145, bolted to the AOTF housing 156 by bolts 156a and 156b. The AOTF housing is shown in cross-section. The AOTF module 158, which contains the AOTF 114 and the transducers 122, lies on a support block 160. The module 158 comes sealed by the manufacturer. It has entrance and exit ports 162 and 164, respectively, to allow the passage of radiation. The ports are 8mm×12mm. Between the support block 160 and the AOTF module 158, is a heater 164, available from Minco Products, Inc. for maintaining the temperature of the AOTF module 158. A thermal sWitch 165 lies beneath the heater 164, within the support block 160, to prevent overheating. The heater with heating coils 164a, is shoWn in greater detail in FIG. 6a. A controller 166 controls the operation of the heater 164. FIG. 6b is a top view of the acousto-optic system 102 with the top of the AoTF housing 156 partially removed, which shows the controller 166 for the heater 164. A temperature sensor 167 is shown in FIG. 7 connected to the heater controller 166. The heater is capable of maintaining the temperature of the crystal within 1. Celsius of the desired temperature, which can be between 40-50° C.

Returning to FIG. 6, a temperature sensor 170 lies inside the AOTF for communicating the temperature of the AOTF 114 to the controller 200. Adjusting screws 172 enable the rotational adjustment of the position of the module 158. The support block 160 lies on the bottom of the housing 156, which is supported by four shock absorbers 176, available from Lord, Inc.

The optic fibers 132a and 132b, shown exiting the exit optical system 145 in FIG. 6b, travel in the same cable (not shown) to the sample cell 200, discussed below. They also travel in the same cable from the sample cell to the detectors. By keeping the optical fibers in close proximity in the same cable, it is expected that any deviations in temperature, for example, which could affect one tuned beam, will similarly affect the other. Therefore, noise in the optical fibers can be effectively corrected.

Figure 8:
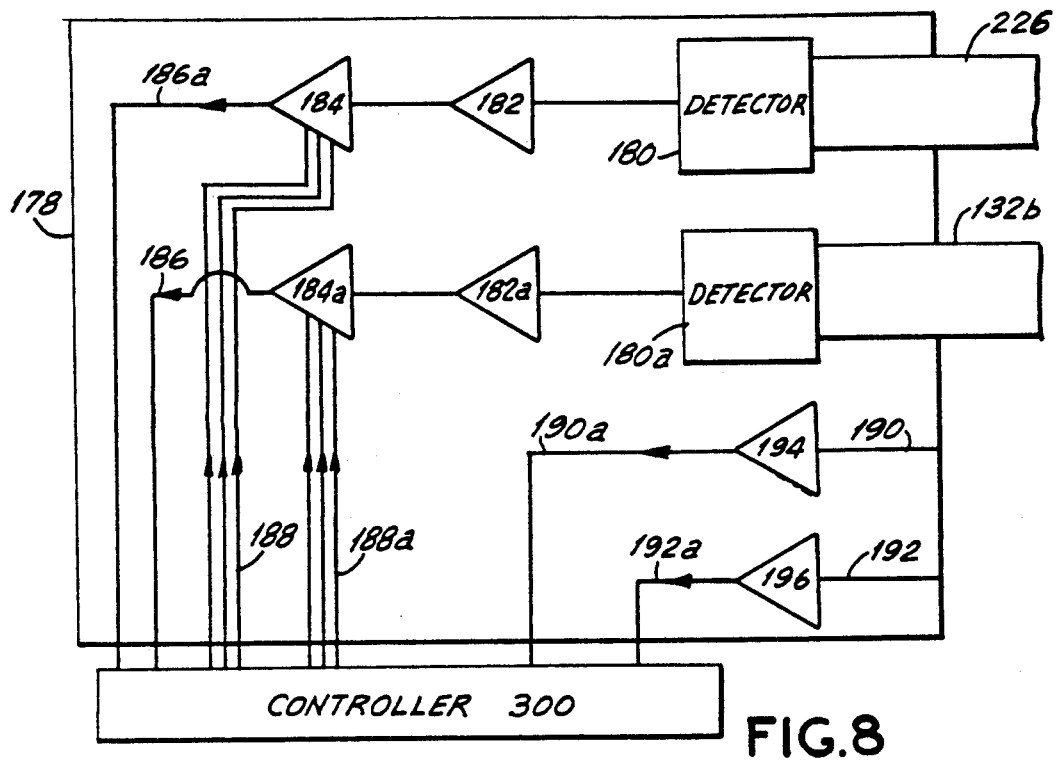
FIG. 8 is a schematic diagram of the analog block shown in FIG. 7.

The electrical components of the electro-optic system 100 are shown in FIGS. 7 and 8. In FIG. 7, the rf amplifier 124 drives the transducers 122 within the optics system 102. A cable 124a is shown in FIG. 6b connected to the AOTF module 158, which carries the output of the rf amplifier to the transducers 122. A 28 volt power supply 124a supplies power to the amplifier 124. The lamp 102 is powered by a 5V poWer supply 102a. The heater 164, thermal sWitch 165 and temperature controller 166 are shown, With their AC power supply 166a. The thermal sensor 170 is shown with it's output leading to the controller.

An analog block 178 is shown with an input 226, which is the optical fiber carrying the radiation beam exposed to the sample. Input 132b is the optical fiber carrying the reference beam. Input 190 is from the temperature sensor 170 in the AOTF module 15B and input 192 is from a temperature sensor 246 in the sample cell 200, discussed below.

Output lines 190a and 192a carrying signals from the temperature sensors 170 and 246 to the controller 300. Output lines 186 and 186a carry information from the optical fibers 226 and 132, as discussed below. The analog block 178 is powered by power supply 178a. The details of the analog block are shown in greater detail in FIGS. 8 and 8a.

In FIG. 8, detectors 180 and 180a, preferably photodiodes of indium gallium arsenide, are shown connected to pre-amplifiers 182 and 182a and variable gain amplifiers 184 and 184a whose outputs 186 and 186a lead to the controller 300 for analysis. The variable gain amplifiers are controlled by the controller 300, through the input lines 188 and 188a. If the signal received by the controller 300 from the variable gain amplifiers 184 or 184a is below a predetermined level, the controller 300 increases the gain of the amplifiers 184, 184a so that the signal is sufficient for resolution. FIG. 8 shows six input lines 188 and 188a from the controller representing the inputs to the variable gain amplifiers. The indium gallium arsenide detectors are available from Epitaxx, Inc., model number ETX 1000 Detectors of germanium may also be used.

Figure 8A:
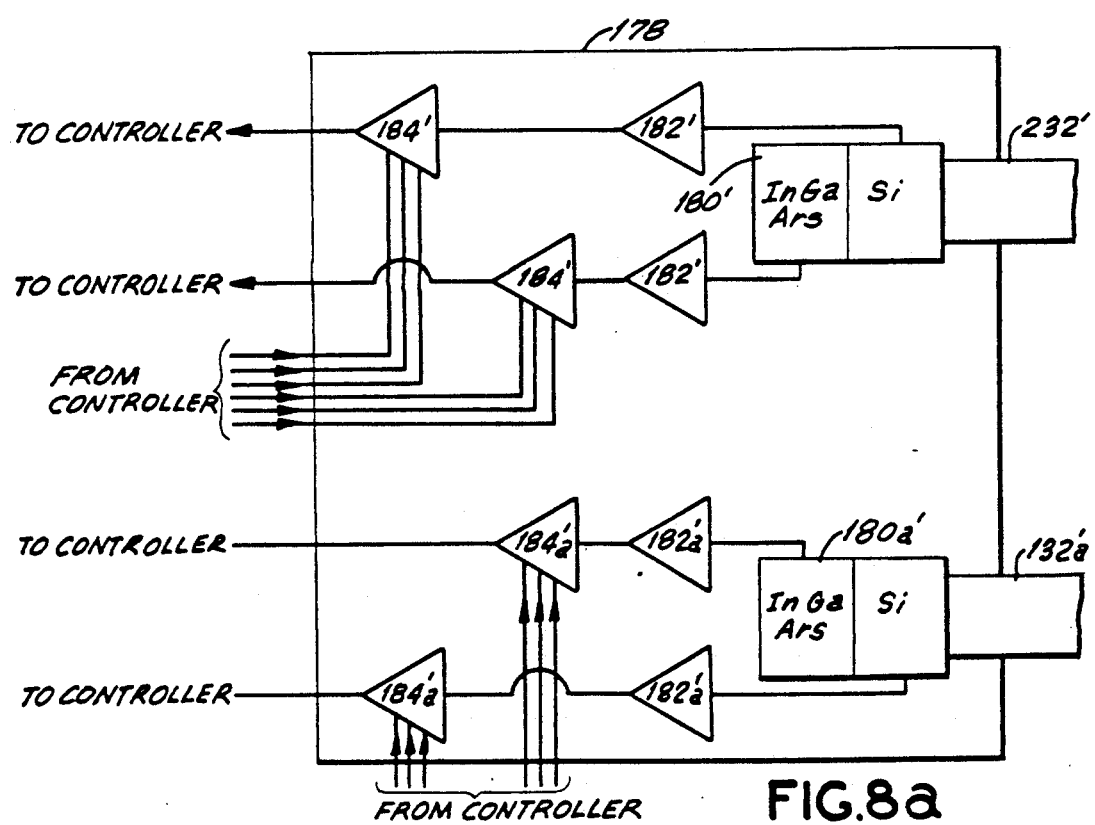
FIG. 8a is a schematic diagram of a preferred embodiment of the analog block in FIG. 7.

Indium gallium arsenide detectors are effective over a range of 900-1700 nanometers. To expand the wavelength range which can be detected by the AOTS 1, it is preferred that a dual detector comprising a sandwich of indium gallium arsenide and silicon, which has an effective range of 400-1,100 nanometers, be used. The detectors are placed in the same photodiode, with the silicon detector on top. To properly match the optical fibers, which have a diameter of about 1 mm, the indium gallium arsenide detector should have a diameter of 1-2 mm while the silicon detector should have a diameter of 2-3 mm. Such a dual detector is also available from Epitaxx, Inc., model number 2000 si. A partial schematic of the circuitry for use with a dual detector is shown in FIG. 8a, with corresponding elements numbered with primes.

The detectors are positioned on the same aluminum mount on the analog card corresponding to analog block 178. Since they are in the same environment, their temperatures are about the same. For greater precision, a temperature controller can be provided to maintain the temperature of the detectors at the same level.

Also shown in FIG. 8 is the input 190 from the temperature sensor 170 on the AOTF module 158 and input 192 from the temperature sensor from the sample cell 200, discussed below. These inputs are amplified by amplifiers 194 and 196, whose Outputs lead to the controller 300.

The Liquid Cell

Figure 9:
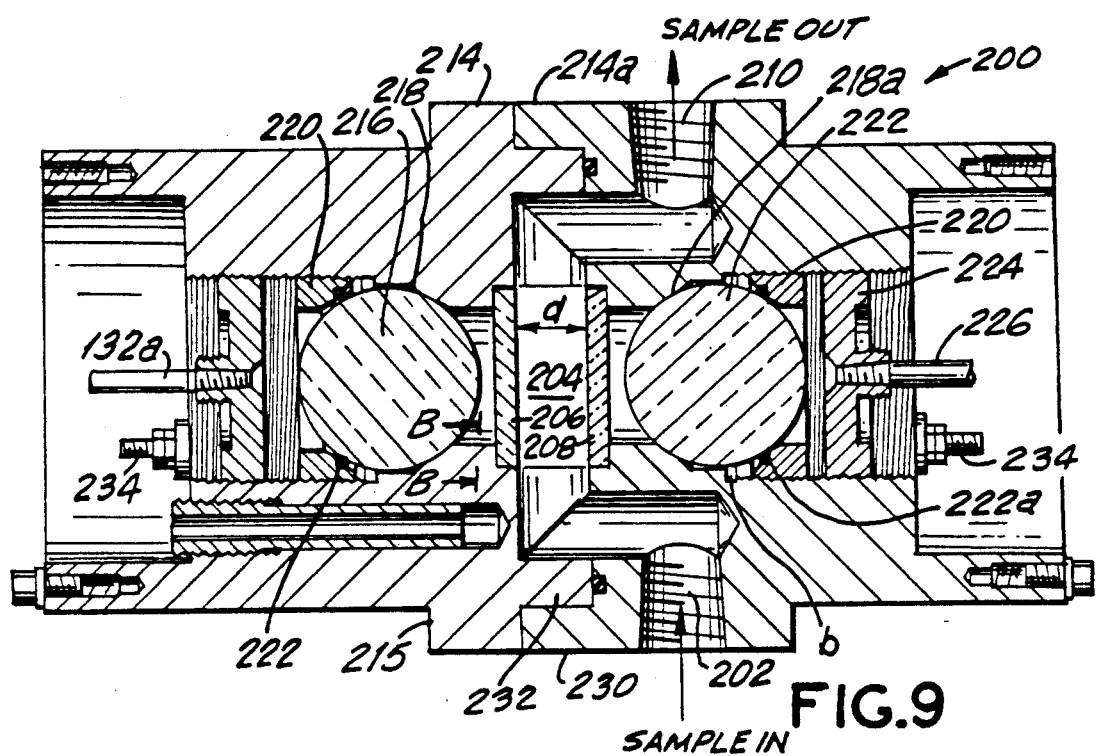
FIG. 9 is a cross-sectional view of liquid cell of the present invention.

The liquid cell 200 of the present invention has a unique design with wide applicability. FIG. 9 shows a cross-sectional view of the cell 200, which has two main parts, housings 214 and 214a. The sample to be tested enters the cell through a tube at 202. The pathway makes two 90° turns to bring the sample into the analysis area 204, where it is exposed to a tuned beam. The analysis area is bounded by two transparent parallel windows 206 and 208 which are preferably sapphire discs. The pathway makes two additional 90° turns to exit the sample cell at 210. It is preferred that the sample travel upward to avoid the formation of bubbles.

Radiation for testing the sample enters the cell 200 through the fiber optic cable 132a attached to a front fiber optic coupling 212. The coupling screws into a threaded section 215 of the cell housing 214 and its position is adjustable by rotation. To ensure that the radiation is incident upon the sample, the radiation needs to be collimated. This also eases the collection of the radiation after its interaction with the sample. In prior art sample cells, collimating lens have been used. It has been found, however, that a properly sized glass ball 216 can provide collimation equal to or better than conventional lenses, at lower cost. Furthermore, the assembly of the sample cell 200 is easier with glass balls than lenses, since there are no orientation problems. The ball can be simply placed in position, supported by the shoulder 218 of the cell housing 214. A retainer 220 secures the ball 216 in position and an 0-ring seal 222 prevents the seepage of sample if there is a leak. In the present application, the glass ball has a diameter of about 25.4 mm. The optimum size ball for this size optical fiber was determined by an optical ray tracing program such as Optec II by Scioptics. Suitable balls are available from Imetra, Inc.

The collimated light passes through the first sapphire disc 206 and interacts with the sample. Radiation transmitted or scattered by the sample passes through the second sapphire disc 208, and through a second glass ball 222 which is identical to the first. The glass ball 222 focuses the radiation into a collecting means, preferably the fiber optic cable 226 in the coupling 224. The glass ball 218 rests against the shoulder 218a of housing 214a. It is secured in position by retainer 220 and is sealed by O-ring 222a.

The housings 214 and 214a are bolted together through shoulders 215 and 230. The two housings can be easily separated, exposing the analysis area 204 and sample flow paths 202 and 210 for direct cleaning. This is a major advantage over the prior art sample cells, which can generally be cleansed only by flushing the sample flow path. An 0-ring seal 228 seals the sample cell from leakage between the housings.

The depth "d" of the analysis area 204 depends on the sample to be tested, and can vary between about 0.10mm-100 mm, depending on the sample. A narrower cell is preferred for samples such as cheese or chocolate, which cause excessive diffusion preventing the collection of sufficient radiation to determine useful information. For beer or organic compounds such as gasoline, which do not diffuse sufficient radiation to interfere with an analysis, a larger sample cell size would be preferred. The sample cell can be easily manufactured in different sizes merely by varying the heights of shoulders 230 and 232.

The sample cell of the present invention includes leak detectors 234, which detect the leakage of sample across the sapphire discs 206 and 238. The top of the detectors are shown in FIG. 9.

Figure 9A:
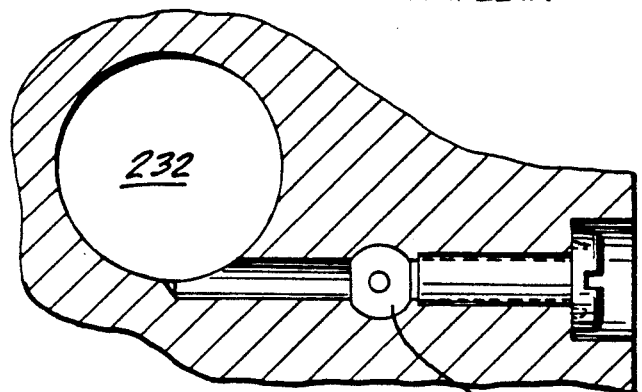
FIG. 9a is a view along line B—B in FIG. 8.
Figure 9B:
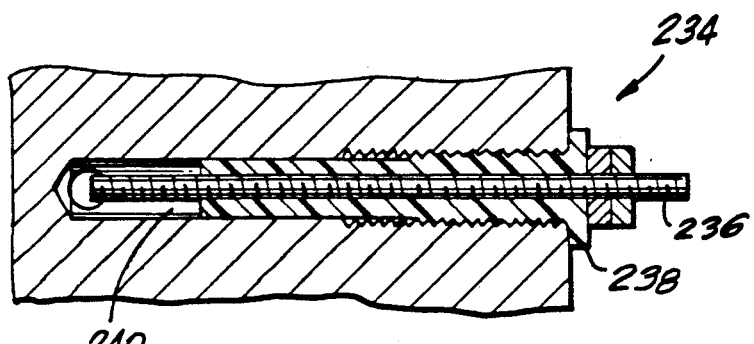
FIG. 9b is a cross sectional view of the leak detector used in the liquid cell.

FIG. 9a shows a cross-section of the leak detector 234, which consists of a threaded steel rod 236 surrounded by a plastic bushing 238. The rod 236 and bushing 238 lie in a shaft 240 in communication with the region "b". FIG. 9b is a view along line B—B in FIG. 9, showing region b. A wire from the electro-optic system 100 is attached to a bolt 242 screwed to the top of the rod 236, in an open circuit. If sample leaks into the shaft 240 and contacts the rod 236, the rod will be short circuited. This will be detected by the controller 300, as discussed below. The controller 300 can indicate that there is a leak through a light or an alarm, for example.

The sample cell 200 also includes a temperature sensor 246, which is connected to the controller 30 through the electro-optic system 100. See FIG. 7. Variations in the temperature of the sample can effect its absorbance, and the controller can correct for this by adjusting the absorbance readings or changing the constant in the concentration equation, which is discussed below.

Figure 10:
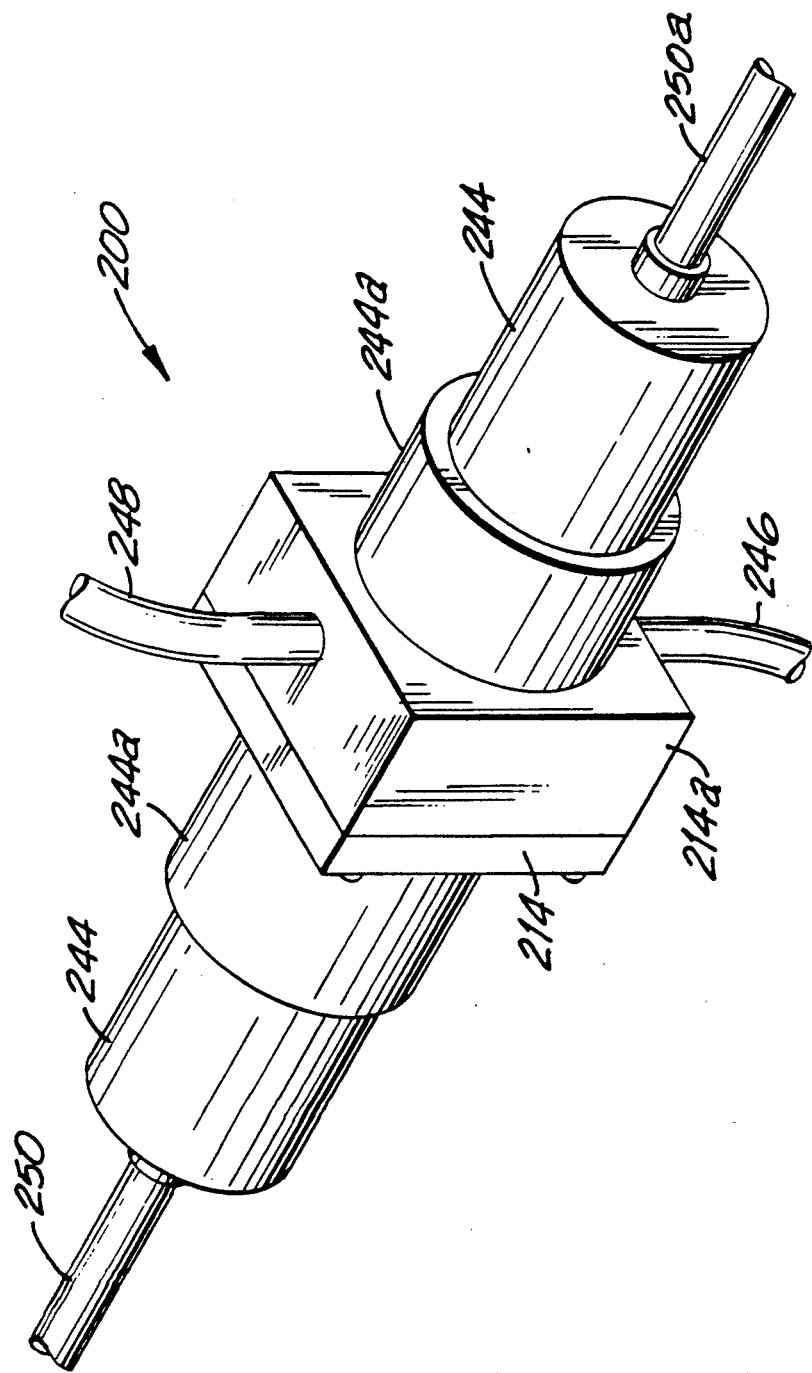
FIG. 10 is a side view of the exterior of the liquid cell of the FIG. 9.

FIG. 10 is an exterior side view of the sample cell 200 of the present invention. A cable 250 carries the optical fibers 132a and 132b. Optical fiber 132b bypasses the sample cell, while optical fiber 132a enters the cell. Cable 250a carries optical fiber 226 and 132b to the detectors 180 and 180a. By enclosing the optical fibers within the same cable, the temperature of the fibers can be maintained essentially the same. The cable 250 is surrounded by protective metal collars 244 and 244a.

The sample cell is a discrete unit which can be easily moved and connected to a sample stream. It is adapted for in-line monitoring of samples during a manufacturing process, for example. The sample cell may be any desired distance from the electrooptics system 100 or the controller 300. This is often desireable to separate the sample cell 200 from the rest of the system when dealing with hazardous samples, such as gasoline.

The Controller

Figure 11:
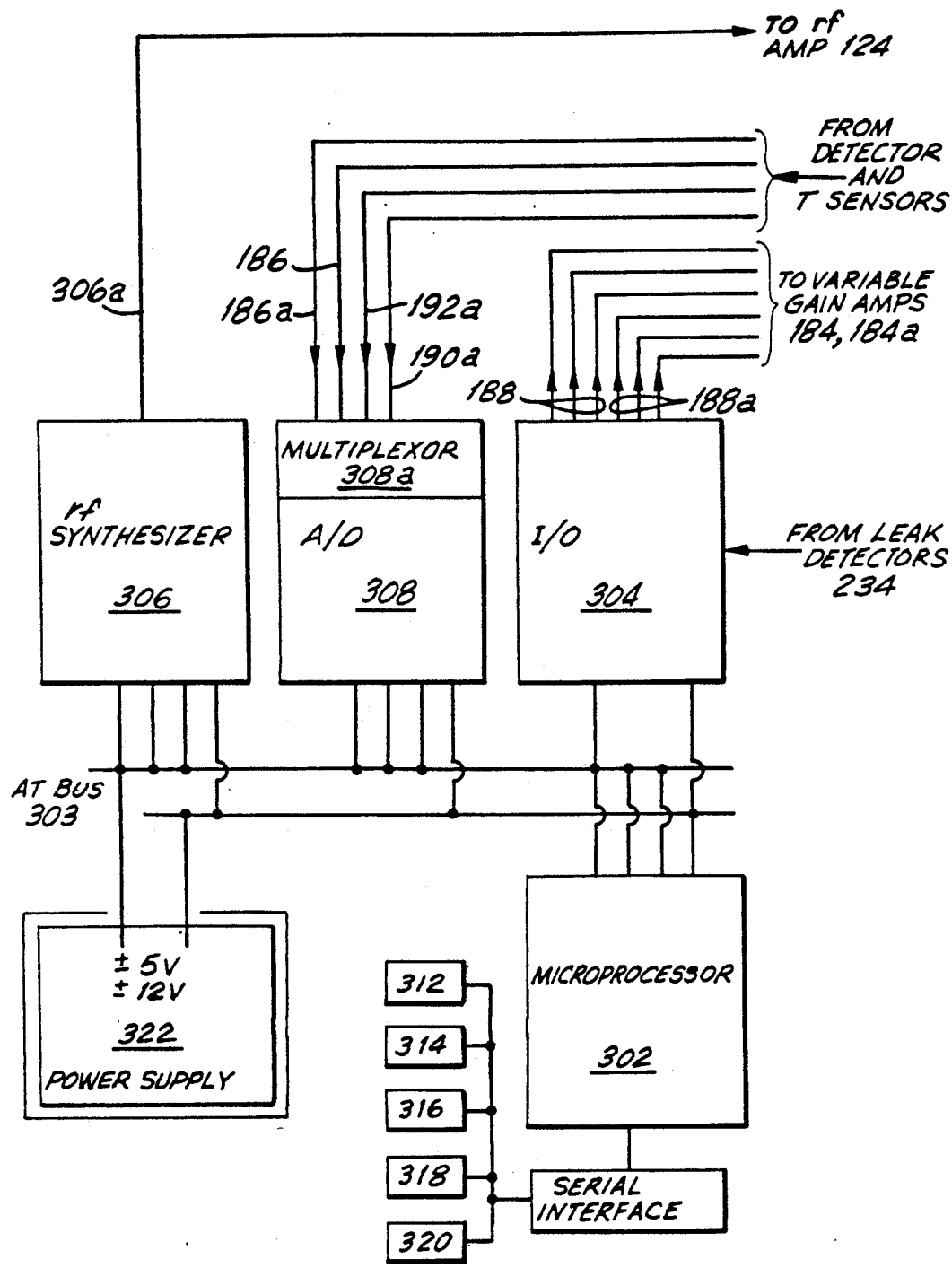
FIG. 11 is a schematic view of the controller used in the present invention.

The controller 300 comprises a microprocessor 302, an input/output circuit 304, an rf synthesizer 306 and an analog/digital convertor 308 with a multiplexor 308a, shown schematically in FIG. 11. Power supply 322 is also shown. Each of these elements communicate with each other through the AT BUS 303. The microprocessor 302, such as the Intel 80286 or 80386, with an optional coprocessor 80287 or 80387, controls the AOTF 114 through the digital input/output circuit 304 and the rf synthesizer 306. The output 306a of the rf synthesizer 306 is amplified by the rf amplifier 124 in the electro-optic system 100. See FIG. 7. The input/output circuit 304 is an IBM compatible digital input/output card available from Industrial Computer Source, for example.

Information is input to the microprocessor 302 from the electro-optic system 200 through the multiplexor 308a of the analog/digital converter 308. Four inputs are shown. 186 and 186a are from the detectors, 180 and 180a. 192 and 192a are from used, there would be two additional inputs to the multiplexor 308a. The analog/digital converter is a 16 bit, IBM compatible analog/digital converter card that includes a multiplexor, available, for example, from Analog, Devices Inc.

The microprocessor 302 controls the variable gain amplifiers 184, 184a in the analog block 174 through the digital input/output circuit 304, as well. If the signals received by the microprocessor 302 from the detectors 180, 180a, are too low for adequate resolution, the microprocessor 302 increases the gain of the variable gain amplifiers 184, 184a. If the dual detectors are used, there would be six additional outputs to the variable gain amplifiers. The digital input/output circuit 304 can also detect a short circuit in the leak detector 234 and inputs this information to the microprocessor 302.

An instrument display 312 for indicating concentration percentages and an instrument keypad 314 for remote access to the controller are included. They are connected to the microprocessor through a serial interface, such as an RS232 or RS422, available from Metrabyte. A power supply 322 is also shown.

Optionally, a ROM 16 can be included for start up without a floppy disk. Alternatively, a hard drive 318 can be included. Other options include a keyboard 320 for programming and a video display 322.

To drive the AOTF 114 at a particular frequency to tune a particular wavelength band, the microprocessor 302 generates a 24 bit binary number chosen from a table. It could also be determined by an equation. This number is input to the rf synthesizer 306 through the input/output circuit 304. The rf synthesizer 306 preferably consists of a low frequency synthesizer 324 and a high frequency phase lock loop circuit 326, as shown in FIG. 11a. The phase lock loop circuit 326 consists of a voltage controlled oscillator ("VCO") 328, a frequency divider 330, a phase detector 332 and a filter 334.

The low frequency rf synthesizer 306a is a Model DDS from A & A Engineering, which can generate a frequency up to about 6.5 MHz. Frequencies from about 75 to 200 MHz are required to drive the AOTF 114, however, therefore, a phase lock loop circuit 324 is used to generate the necessary frequency. The VCO 328 generates a high frequency between 75-200 MHz, which is divided by 64 in the frequency divider 330. The output of the frequency divider 330 is within the frequency range of the low frequency synthesizer 306a. The phase detector 332 compares the frequency from the rf synthesizer 306a and the frequency divider 330. If there is a difference, the VCO 328 is adjusted until it matches. The rf output 336 of the VCO 328 leads to the rf switch 338, which is controlled by the microprocessor 302 through the input/output circuit 304. The signal from the rf switch 302 is amplified by the rf amplifier 124 in the electro-optic system 100, to drive the AOTF 124. The VCO 328 can be a Motorola MC1648. The phase detector 332 can be a Motorola 4044, with an upper limit of 8MHz.

A high frequency synthesizer could be used instead of the low frequency synthesizer and phase lock loop, but it would be much more expensive. The present system is accurate within about 100 hertz and is very fast, allowing for switching between frequencies in less than about 100 microseconds and as fast as about 30 microseconds.

In operation, the AOTS 1 analyzes a sample across a schedule of wavelengths called a scan. The scan can comprise several key wavelengths or the full spectrum between about 800-1700 nm, depending on the application and needs of the user. A scan of random wavelengths can also be performed. As discussed above, the microprocessor 302 generates a 24 bit binary code which is converted into a frequency by the rf synthesizer 306. This frequency drives the AOTF, tuning it to select the particular wavelength band which will be applied to the sample. After testing, another 24 bit code is generated, corresponding to the next frequency, and thus the next wavelength band. This repeats until all the codes corresponding to the wavelengths to be tested in a scan have been generated. Usually, about 20 wavelengths are tested in a scan, which can be performed as fast as 0.001 seconds.

Over a scan, noise can account for about 150 micro-optical density. To improve precision, a scan is preferably repeated 100 times and the results are averaged. Over 100 scans, the effect of noise drops to about 30 micro-optical density. 100 scans can be repeated in about 0.10 seconds. This is much faster than the scan rate of prior art mechanical spectrometers. The wavelength repeatability from scan to scan is without about 0.05 nanometers.

The controller 302 receives voltage readings from the detectors 180 and 180a, of the sample and reference beams. The controller 302 also receives voltage readings from the detectors when the system is at rest and no beam is received. These "darkfield" values are subtracted from the voltage reading of the beams to correct for scattered light which may leak into the system. The logarithm of the corrected voltage of the reference detector is divided by the corrected voltage of the sample detector, to determine the absorbance, or optical density of the sample at a particular wavelength, as shown in the equation below:

$$L = \text{Log}\left[\frac{Vrd - Vrdr}{Vsd - Vsdr}\right]$$

where L is the optical density or absorbance, Vrd is the voltage of the reference detector during a reading, Vrdr is the voltage of the reference detector at rest, Vsd is the voltage of the sample detector during a reading and Vsdr is the voltage of the sample detector at rest. The rest readings are usually the first readings of each scan.

From the absorbance of the sample at each wavelength, the concentration of a component can be determined according to the equation below:

$$(\%) = B_0 + B_1 L_1 + B_2 L_2 + \ldots B_n L_n,$$

where (%) is the concentration of the component of the sample to be measured, $B_O \ldots B_n$ are constants dependent upon the sample and the component of the sample to be measured, and $L_l \ldots L_n$ are equal to the absorbance of the component of the sample at the test wavelengths O...n.

While the sample and reference beams are being simultaneously measured by the detectors 180, 180a, the analog-digital converter 308 which receives the signals from the detector can only process one signal at a time. Therefore, the measurements of the sample and reference beams used to determine the absorbance are several microseconds apart. This is too small a time difference to effect the accuracy of the readings. A dual channel A/D converter could be used but this would increase the cost of the AOTS.

In addition to the corrections for noise by the reference and rest measurements, corrections for variations in the temperature of the AOTF 114 could also be required. The temperature controller 166 and heater 164 can maintain the temperature of the crystal within ±1° Celsius. However, deviations within one degree can slightly alter the wavelength band of the tuned beams. The microprocessor 302, therefore, may generate a different 24 bit code to generate a different driving frequency on the AOTF 114, depending on the temperature signal from the temperature sensor.

Another potential source of error is the acoustic resonance caused by the reflection of the acoustic wave off the end of the crystal opposite the transducers. The reflection interferes with the primary acoustic waves generated by the transducers, setting up a resonance pattern which changes the wavelength band of the incident radiation which is tuned. There are various ways to minimize this resonance, such as roughening the far end of the crystal or providing an acoustic absorber, but some reflection remains.

The effect of this reflection is shown in FIG. 12, which is a graph of the driving frequency applied to the crystal versus the intensity of the signal at a detector with no sample present. The curve consists of high frequency oscillations 3 which are nearly sinusoidal, referred to as acoustic resonant fringes. These resonances can introduce an error of up to about 10% in absorbance. Intensity should vary smoothly with frequency, as shown in FIG. 12a. The dip 5 in the graph is due to the absorbance of the optical fiber itself.

One way to correct for acoustic resonance is to test absorbencies at many closely spaced points and average the resulting curve. This can be time consuming. It has been found that an average of the intensity one-quarter wavelength of the acoustic resonance above and below the desired frequency accurately approximates the actual intensity.

The currently preferred approach is to average the intensity at a given frequency with the intensity at that frequency plus one-half of the wavelength of an acoustic resonance. This value can also be determined by the manufacturer of the crystal, based on the crystal's characteristics.

The unique optical design and the many corrections performed by the control system enables the AOTS of the present invention to be faster, more accurate and more precise than prior art analyzing systems. Nearly simultaneous evaluation of a sample across the spectrum of interest is possible. The system is ideally suited for in-line monitoring of flowing samples in industrial processes.

We claim:

1. A dual beam acousto-optic tunable spectrometer comprising;
   a radiation source;
   a birefringent acousto-optic tunable filter;
   means for driving said acousto-optic tunable filter at a desired frequency such that radiation incident upon said filter is tuned to a first and second beam diverging from each other and the radiation outside the tuned bandwidth;
   means for collecting said first tuned beam for use in analyzing a sample; and
   means for collecting said second beam for use as a reference.

2. An acousto-optic tunable spectrometer comprising:
   a radiation source;
   means for collimating radiation from said radiation source;
   an acousto-optic tunable filter;
   means for driving said acousto-optic tunable filter at particular frequencies such that desired narrow bandwidths of radiation incident on said acousto-optic tunable filter will be tuned, said tuned bandwidth forming a first and second tuned beam which diverge from each other and the radiation outside said narrow bandwidth;
   means for conveying said first tuned beam to a sample;
   first detector means for detecting said first tuned beam after exposure to said sample;
   second detector means for detecting said second tuned beam for use as a reference;
   means for conveying said second tuned beam to said second detector;
   analyzing means; and
   means for inputing signals from said first and second detecting means to said analyzing means.

3. The spectrometer of claim 2, wherein said means for collimating radiation comprises a collimating lens.

4. The spectrometer of claim 3, wherein said tuned beams have an angle of diffraction upon exiting said acousto-optic tunable filter and said collimating lens has a field angle less than onehalf of said angle of diffraction.

5. The spectrometer of claim 3, further comprising condensing means between said radiation source and said collimating lens for collecting radiation from said radiation source.

6. The spectrometer of claim 5, wherein said condensing means comprises a pair of plano-convex lenses and a first aperture, said lenses focusing said radiation on said first aperture, said aperture defining the angular divergence of the radiation incident upon said collimating lens.

7. The spectrometer of claim 3, further comprising a first aperture between said source of radiation and said collimating lens for defining the angular divergence of the radiation incident upon said collimating lens.

8. The spectrometer of claim 6, further comprising a second aperture between said collimating lens and said acousto-optic tuned filter, said second aperture defining the size of the radiation beam incident upon the acousto-optic tunable filter.

9. The spectrometer of claim 8, wherein the size of the radiation beam incident upon the acousto-optic filter is slightly less than the size of the acousto-optic filter, such that the radiation beam incident upon the acousto-optic filter is not scattered prior to entering the filter.

10. The spectrometer of claim 3, further comprising a disc defining first and second tuned beam apertures, said first aperture for receiving said first tuned beam and said second aperture for receiving said second tuned beam, said disc further comprising a central region for absorbing said non-tuned radiation.

11. The spectrometer of claim 10, further comprising an achromatic lens system for collecting said radiation exiting said acousto-optic tunable crystal and focusing said first tuned beam on said first tuned beam aperture, focusing said second tuned beam on said second tuned beam aperture and focusing said nontuned beam on said central region of said disc.

12. The spectrometer of claim 11, wherein said achromatic lens system comprises an achromatic objective lens and an aplanatic meniscus lens.

13. The spectrometer of claim 10, wherein said means for conveying said first and second tuned beams comprises optical fibers, said spectrometer further comprising first and second condensing systems for collecting said first and second tuned beams received by said first and second tuned beam apertures, said first and second condensing systems focusing said first and second beams into said first and second optical fibers.

14. The spectrometer of claim 13, further comprising a cable for carrying said first and second optical fibers.

15. The spectrometer of claim 14, wherein said means for conveying said beam to said sample is an optical fiber.

16. The spectrometer of claim 3, further comprising a sample cell for holding said sample.

17. The spectrometer of claim 16, wherein said sample cell comprises a sample analysis area and a glass ball for collimating said first tuned beam on said sample analysis area.

18. The spectrometer of claim 17, wherein said sample cell comprises a glass ball for focusing radiation exposed to said sample on a collecting means.

19. The spectrometer of claim 18, wherein said collecting means is an optical fiber.

20. The spectrometer of claim 16, wherein said sample cell is remotely located from said system.

21. The spectrometer of claim 16, wherein said sample cell includes a leak detector.

22. The spectrometer of claim 16, wherein said sample cell includes a temperature sensor.

23. The spectrometer of claim 3, further comprising a sample cell for containing a sample to be tested, wherein said means for exposing said first tuned beam to a sample is a first optical fiber carrying said first tuned beam to said sample cell, said spectrometer further comprising a third optical fiber for conveying said first tuned beam from said sample cell to said first detector means.

24. The spectrometer of claim 23, wherein said first and second detector means comprise indium gallium arsenide or germanium.

25. The spectrometer of claim 24, wherein said first and second detectors further comprise silicon.

26. The spectrometer of claim 3, wherein said means for driving said acousto-optic tunable filter comprises a controller and transducer means in contact with said acousto-optic tunable filter, said transducer means controlled by said controller.

27. The spectrometer of claim 26, wherein said controller comprises a microprocessor for generating a code corresponding to a desired driving frequency of said acousto-optic tunable filter and a rf synthesizer for converting said code into a frequency for driving said transducer.

28. The spectrometer of claim 27, wherein said rf synthesizer comprises a low frequency synthesizer and a phase lock loop circuit for generating the frequency required to drive said transducer.

29. The spectrometer of claim 28, wherein said microprocessor accounts for deviations in the temperature of said acousto-optic tunable filter by generating a different code for driving said acousto-optic tunable filter at said desired frequency.

30. The spectrometer of claim 26, wherein said controller comprises a microprocessor.

31. The spectrometer of claim 30, wherein said microprocessor averages measurements to correct for acoustic resonances.

32. The spectrometer of claim 31, wherein said measurements are made in equal acoustic resonance wavelength increments above and below the desired frequency.

33. The spectrometer of claim 31, wherein said wavelength increment is one-quarter.

34. The spectrometer of claim 32, wherein one of said measurements is at the desired frequency and the other is onehalf acoustic resonance wavelength increment above the desired frequency.

35. The spectrometer of claim 27, wherein said microprocessor measures the signal at said detectors before generating a driving frequency, said measurements being used to correct subsequent sample and reference measurements.

36. An acousto-optic tunable spectrometer comprising;
  a radiation source;
  a collimating lens;
  a first aperture between said radiation source and said collimating lens defining an angular divergence of radiation from said collimating lens;
  a birefringent acousto-optic tunable filter for tuning a narrow bandwidth of incident radiation into a first and second tuned beam diverging from each other and the non-tuned radiation;
  a microprocessor for determining a frequency for driving said acousto-optic tunable filter;
  a second aperture between said acousto-optic tunable filter and said collimating lens, defining the boundary of the radiation incident on said acousto-optic tunable filter;
  an achromatic lens system for focusing said first and second tuned beams onto a first and second aperture;

first and second optical fibers for collecting said tuned beams;

means for focusing said first and second beams from said first and second apertures into said first and second optical fibers;

a fluid sample cell including an analysis area bounding the sample to be analyzed, said first optical fiber attaching to said sample cell and providing said first tuned beam for analyzing said sample and means for collecting radiation transmitted and scattered by said sample and focusing said sample radiation on a third optical fiber;

a first detecting means for detecting said sample signal from said third optical fiber;

a second detecting means for detecting said second tuned beam from said second optical fiber;

means for conveying detected signals from said first and second detecting means to said microprocessor for analysis.

37. A method for the spectroscopic analysis of fluid samples comprising;

emitting infrared radiation;

collimating said radiation;

exposing said radiation to a birefringent acoustooptical tunable filter;

driving said acousto-optic tunable filter at a desired frequency to tune a specific narrow bandwidth of said radiation yielding a first and second diverging tuned beam;

isolating said first and second tuned beam from each other and the non-tuned radiation;

separately collecting raid first and second tuned beam;

applying said first tuned beam to a sample;

collecting the radiation transmitted and scattered by said sample;

detecting the collected radiation;

detecting the second tuned beam; and determining the absorbance of the sample at the wavelength based on the value of the detected collected radiation and the value of the detected second tuned beam.

* * * * *